United States Patent [19]

Van Broeckhoven et al.

[11] Patent Number: 5,525,714
[45] Date of Patent: Jun. 11, 1996

[54] MUTATED FORM OF THE β-AMYLOID PRECURSOR PROTEIN GENE

[75] Inventors: Christine Van Broeckhoven; Jean-Jacques Martin; Lydia Hendriks; Patrick Cras, all of Antwerpen, Belgium

[73] Assignee: N. V. Innogenetics S.A., Ghent, Belgium

[21] Appl. No.: 133,248

[22] Filed: Oct. 8, 1993

[30] Foreign Application Priority Data

Mar. 20, 1992 [EP] European Pat. Off. ............ 92400771

[51] Int. Cl.⁶ ........................... C07H 21/02; C07H 21/04
[52] U.S. Cl. ...................................... 536/23.5; 536/24.31
[58] Field of Search ..................... 435/6, 320.1; 935/77, 935/78; 536/23.2, 23.5

[56] References Cited

FOREIGN PATENT DOCUMENTS

| WOA8906689 | 7/1989 | WIPO . |
| WOA8907657 | 8/1989 | WIPO . |
| WOA9014840 | 12/1990 | WIPO . |

OTHER PUBLICATIONS

Chemical Abstracts, vol. 117, No. 17, Columbus, Ohio, US; abstract No. 168786w, Murrell, Jill; Farlow, Martin; Ghetti, Bernardino; Benson, Merrill D. "A Mutation in the Amyloid Precursor Protein Associated with Hereditary Alzheimer's Disease".

Science, vol. 248, No. 4959, 1990, Lancaster, PA US, pp. 1124–1126, E. Levy et al, "Mutation of the Alzheimer's Disease . . . ".

Gene, vol. 87, No. 2, Mar. 1990, Amsterdam, NL, pp. 257–263, Shun–Ichi Yoshikai et al, "Genomic Organization . . . ".

Biochemical and Biophysical Research Communications, vol. 178, No. 3, 1991, Duluth Minnesota US, pp. 1141–1146, Katsuji Yoshioka et al, "The 717 Val . . . ".

Hendriks et al Nature genetics 1: 218–221 (1992).

Sommer et al Nucleic Acid Res (1989) 17: 6749.

Lewis Science 237: 1570 (1987).

Webster's Dictionary, II, 1984 p. 589.

Kamino et al, Am J. Hum. Genet. (1992) 51: 998–1014.

*Primary Examiner*—W. Gary Jones
*Assistant Examiner*—Eggerton Campbell
*Attorney, Agent, or Firm*—Nixon & Vanderhye

[57] ABSTRACT

The invention relates to a polypeptide containing a sequence of contiguous amino acids of the polypeptide sequence coded by exon 17 of the cDNA of the APP 770 gene, with said sequence of contiguous amino acids being such that:

it has from 5 to the total number of amino acids coded by said exon 17, and it contains the amino acid corresponding to codon 692 in the cDNA of the APP 770 gene and which is alanine substituted for glycine. (no figure).

20 Claims, 8 Drawing Sheets

FIG. 4A

```
         10        20        30        40        50        60
          |         |         |         |         |         |
ATGCTGCCCGGTTTGGCACTGCTCCTGCTGGCCGCCTGGACGGCTCGGGCGCTGGAGGTA
METLeuProGlyLeuAlaLeuLeuLeuAlaAlaTrpThrAlaArgAlaLeuGluVal 70        80        90       100       110       120
          |         |         |         |         |         |
CCCACTGATGGTAATGCTGGCCTGCTGGCTGAACCCCAGATTGCCATGTTCTGTGGCAGA
ProThrAspGlyAsnAlaGlyLeuLeuAlaGluProGlnIleAlaMETPheCysGlyArg 130       140       150       160       170       180
          |         |         |         |         |         |
CTGAACATGCACATGAATGTCCAGAATGGGAAGTGGGATTCAGATCCATCAGGGACCAAA
LeuAsnMETHisMETAsnValGlnAsnGlyLysTrpAspSerAspProSerGlyThrLys 190       200       210       220       230       240
          |         |         |         |         |         |
ACCTGCATTGATACCAAGGAAGGCATCCTGCAGTATTGCCAAGAAGTCTACCCTGAACTG
ThrCysIleAspThrLysGluGlyIleLeuGlnTyrCysGlnGluValTyrProGluLeu 250       260       270       280       290       300
          |         |         |         |         |         |
CAGATCACCAATGTGGTAGAAGCCAACCAACCAGTGACCATCCAGAACTGGTGCAAGCGG
GlnIleThrAsnValValGluAlaAsnGlnProValThrIleGlnAsnTrpCysLysArg 310       320       330       340       350       360
          |         |         |         |         |         |
GGCCGCAAGCAGTGCAAGACCCATCCCCACTTTGTGATTCCCTACCGCTGCTTAGTTGGT
GlyArgLysGlnCysLysThrHisProHisPheValIleProTyrArgCysLeuValGly 370       380       390       400       410       420
          |         |         |         |         |         |
GAGTTTGTAAGTGATGCCCTTCTCGTTCCTGACAAGTGCAAATTCTTACACCAGGAGAGG
GluPheValSerAspAlaLeuLeuValProAspLysCysLysPheLeuHisGlnGluArg
```

FIG. 4B

```
         430       440       450       460       470       480
          |         |         |         |         |         |
ATGGATGTTTGCGAAACTCATCTTCACTGGCACACCGTCGCCAAAGAGACATGCAGTGAG
METAspValCysGluThrHisLeuHisTrpHisThrValAlaLysGluThrCysSerGlu 490       500       510       520       530       540
          |         |         |         |         |         |
AAGAGTACCAACTTGCATGACTACGGCATGTTGCTGCCCTGCGGAATTGACAAGTTCCGA
LysSerThrAsnLeuHisAspTyrGlyMETLeuLeuProCysGlyIleAspLysPheArg 550       560       570       580       590       600
          |         |         |         |         |         |
GGGGTAGAGTTTGTGTGTTGCCCACTGGCTGAAGAAAGTGACAATGTGGATTCTGCTGAT
GlyValGluPheValCysCysProLeuAlaGluGluSerAspAsnValAspSerAlaAsp 610       620       630       640       650       660
          |         |         |         |         |         |
GCGGAGGAGGATGACTCGGATGTCTGGTGGGGCGGAGCAGACACAGACTATGCAGATGGG
AlaGluGluAspAspSerAspValTrpTrpGlyGlyAlaAspThrAspTyrAlaAspGly 670       680       690       700       710       720
          |         |         |         |         |         |
AGTGAAGACAAAGTAGTAGAAGTAGCAGAGGAGGAAGAAGTGGCTGAGGTGGAAGAAGAA
SerGluAspLysValValGluValAlaGluGluGluGluValAlaGluValGluGluGlu 730       740       750       760       770       780
          |         |         |         |         |         |
GAAGCCGATGATGACGAGGACGATGAGGATGGTGATGAGGTAGAGGAAGAGGCTGAGGAA
GluAlaAspAspAspGluAspAspGluAspGlyAspGluValGluGluGluAlaGluGlu 790       800       810       820       830       840
          |         |         |         |         |         |
CCCTACGAAGAAGCCACAGAGAGAACCACCAGCATTGCCACCACCACCACCACCACCACA
ProTyrGluGluAlaThrGluArgThrThrSerIleAlaThrThrThrThrThrThrThr 850       860       870       880       890       900
          |         |         |         |         |         |
GAGTCTGTGGAAGAGGTGGTTCGAGAGGTGTGCTCTGAACAAGCCGAGACGGGGCCGTGC
GluSerValGluGluValValArgGluValCysSerGluGlnAlaGluThrGlyProCys
```

FIG. 4C

```
          910       920       930       940       950       960
           |         |         |         |         |         |
    CGAGCAATGATCTCCCGCTGGTACTTTGATGTGACTGAAGGGAAGTGTGCCCCATTCTTT

ArgAlaMETIleSerArgTrpTyrPheAspValThrGluGlyLysCysAlaProPhePhe 970       980       990      1000      1010      1020
           |         |         |         |         |         |
    TACGGCGGATGTGGCGGCAACCGGAACAACTTTGACACAGAAGAGTACTGCATGGCCGTG

TyrGlyGlyCysGlyGlyAsnArgAsnAsnPheAspThrGluGluTyrCysMETAlaVal 1030      1040      1050      1060      1070      1080
           |         |         |         |         |         |
    TGTGGCAGCGCCATGTCCCAAAGTTTACTCAAGACTACCCAGGAACCTCTTGCCCGAGAT

CysGlySerAlaMETSerGlnSerLeuLeuLysThrThrGlnGluProLeuAlaArgAsp 1090      1100      1110      1120      1130      1140
           |         |         |         |         |         |
    CCTGTTAAACTTCCTACAACAGCAGCCAGTACCCCTGATGCCGTTGACAAGTATCTCGAG

ProValLysLeuProThrThrAlaAlaSerThrProAspAlaValAspLysTyrLeuGlu 1150      1160      1170      1180      1190      1200
           |         |         |         |         |         |
    ACACCTGGGGATGAGAATGAACATGCCCATTTCCAGAAAGCCAAAGAGAGGCTTGAGGCC

ThrProGlyAspGluAsnGluHisAlaHisPheGlnLysAlaLysGluArgLeuGluAla 1210      1220      1230      1240      1250      1260
           |         |         |         |         |         |
    AAGCACCGAGAGAGAATGTCCCAGGTCATGAGAGAATGGGAAGAGGCAGAACGTCAAGCA

LysHisArgGluArgMETSerGlnValMETArgGluTrpGluGluAlaGluArgGlnAla 1270      1280      1290      1300      1310      1320
           |         |         |         |         |         |
    AAGAACTTGCCTAAAGCTGATAAGAAGGCAGTTATCCAGCATTTCCAGGAGAAAGTGGAA

LysAsnLeuProLysAlaAspLysLysAlaValIleGlnHisPheGlnGluLysValGlu 1330      1340      1350      1360      1370      1380
           |         |         |         |         |         |
    TCTTTGGAACAGGAAGCAGCCAACGAGAGACAGCAGCTGGTGGAGACACACATGGCCAGA

SerLeuGluGlnGluAlaAlaAsnGluArgGlnGlnLeuValGluThrHisMETAlaArg
```

FIG. 4D

```
          1390      1400      1410      1420      1430      1440
            |         |         |         |         |         |
GTGGAAGCCATGCTCAATGACCGCCGCCGCCTGGCCCTGGAGAACTACATCACCGCTCTG
ValGluAlaMETLeuAsnAspArgArgArgLeuAlaLeuGluAsnTyrIleThrAlaLeu 1450      1460      1470      1480      1490      1500
            |         |         |         |         |         |
CAGGCTGTTCCTCCTCGGCCTCGTCACGTGTTCAATATGCTAAAGAAGTATGTCCGCGCA
GlnAlaValProProArgProArgHisValPheAsnMETLeuLysLysTyrValArgAla 1510      1520      1530      1540      1550      1560
            |         |         |         |         |         |
GAACAGAAGGACAGACAGCACACCCTAAAGCATTTCGAGCATGTGCGCATGGTGGATCCC
GluGlnLysAspArgGlnHisThrLeuLysHisPheGluHisValArgMETValAspPro 1570      1580      1590      1600      1610      1620
            |         |         |         |         |         |
AAGAAAGCCGCTCAGATCCGGTCCCAGGTTATGACACACCTCCGTGTGATTTATGAGCGC
LysLysAlaAlaGlnIleArgSerGlnValMETThrHisLeuArgValIleTyrGluArg 1630      1640      1650      1660      1670      1680
            |         |         |         |         |         |
ATGAATCAGTCTCTCTCCCTGCTCTACAACGTGCCTGCAGTGGCCGAGGAGATTCAGGAT
METAsnGlnSerLeuSerLeuLeuTyrAsnValProAlaValAlaGluGluIleGlnAsp 1690      1700      1710      1720      1730      1740
            |         |         |         |         |         |
GAAGTTGATGAGCTGCTTCAGAAAGAGCAAAACTATTCAGATGACGTCTTGGCCAACATG
GluValAspGluLeuLeuGlnLysGluGlnAsnTyrSerAspAspValLeuAlaAsnMET 1750      1760      1770      1780      1790      1800
            |         |         |         |         |         |
ATTAGTGAACCAAGGATCAGTTACGGAAACGATGCTCTCATGCCATCTTTGACCGAAACG
IleSerGluProArgIleSerTyrGlyAsnAspAlaLeuMETProSerLeuThrGluThr 1810      1820      1830      1840      1850      1860
            |         |         |         |         |         |
AAAACCACCGTGGAGCTCCTTCCCGTGAATGGAGAGTTCAGCCTGGACGATCTCCAGCCG
LysThrThrValGluLeuLeuProValAsnGlyGluPheSerLeuAspAspLeuGlnPro
```

FIG. 4E

```
          1870      1880      1890      1900      1910      1920
            |         |         |         |         |         |
         TGGCATTCTTTTGGGGCTGACTCTGTGCCAGCCAACACAGAAAACGAAGTTGAGCCTGTT

TrpHisSerPheGlyAlaAspSerValProAlaAsnThrGluAsnGluValGluProVal 1930      1940      1950      1960      1970      1980
            |         |         |         |         |         |
         GATGCCCGCCCTGCTGCCGACCGAGGACTGACCACTCGACCAGGTTCTGGGTTGACAAAT

AspAlaArgProAlaAlaAspArgGlyLeuThrThrArgProGlySerGlyLeuThrAsn 1990      2000      2010      2020      2030      2040
            |         |         |         |         |         |
         ATCAAGACGGAGGAGATCTCTGAAGTGAAGATGGATGCAGAATTCCGACATGACTCAGGA

IleLysThrGluGluIleSerGluValLysMETAspAlaGluPheArgHisAspSerGly 2050      2060      2070      2080      2090      2100
            |         |         |         |         |         |
         TATGAAGTTCATCATCAAAAATTGGTGTTCTTTGCAGAAGATGTGGGTTCAAACAAAGGT

TyrGluValHisHisGlnLysLeuValPhePheAlaGluAspValGlySerAsnLysGly 2110      2120      2130      2140      2150      2160
            |         |         |         |         |         |
         GCAATCATTGGACTCATGGTGGGCGGTGTTGTCATAGCGACAGTGATCGTCATCACCTTG

AlaIleIleGlyLeuMETValGlyGlyValValIleAlaThrValIleValIleThrLeu 2170      2180      2190      2200      2210      2220
            |         |         |         |         |         |
         GTGATGCTGAAGAAGAAACAGTACACATCCATTCATCATGGTGTGGTGGAGGTTGACGCC

ValMETLeuLysLysLysGlnTyrThrSerIleHisHisGlyValValGluValAspAla 2230      2240      2250      2260      2270      2280
            |         |         |         |         |         |
         GCTGTCACCCCAGAGGAGCGCCACCTGTCCAAGATGCAGCAGAACGGCTACGAAAATCCA

AlaValThrProGluGluArgHisLeuSerLysMETGlnGlnAsnGlyTyrGluAsnPro 2290      2300      2310
            |         |         |
         ACCTACAAGTTCTTTGAGCAGATGCAGAACTAG

ThrTyrLysPhePheGluGlnMETGlnAsn---
```

MUTATED FORM OF THE β-AMYLOID PRECURSOR PROTEIN GENE

This application is a continuation of PCT/EP 93/00701, filed on Mar. 23, 1993.

The present invention relates to a mutated form of the β-amyloid precursor protein gene.

Alzheimer's disease (AD) is a degenerative disorder of the human central nervous system characterized by progressive impairment of memory and intellectual function, usually beginning in middle to late adult life.

AD produces a progressive neuronal degeneration of selective cells in the association and memory areas of the cerebral cortex, combined with similar abnormalities in certain subcortical nuclei. Neuronal loss especially affects the large pyramidal cells of the hippocampus, the amygdala and the parietal and frontal association area. Histopathologigally, many of the degenerating nerve cells contain tangles of twisted intracellular fibrils of a unique protein configuration related to altered neurofibrillary protein, as well as amyloid plaques and cerebrovascular amyloid deposits comprising extracellular insoluble fibrillar proteins which occur in abnormally large numbers (Wong, C. W., et al., Proc. Natl. Acad. Sci. USA 82:8729 (1985); Hardy, J. A., et al., Neurobiol. Aging 7:489 (1986)). These findings have become a hallmark of the disease.

Recent studies have begun to elucidate the biochemical basis of the disorder. A 42-amino acid peptide has been isolated as the major constituent of brain amyloid plaques and deposits of patients afflicted with AD (Glenner, G. G. and Wong, C. W., Biochem. Biophys. Res. Commun. 122:885 (1984) and Masters, C. L., et al., Proc. Natl. Acad. Sci. USA 82:4245 (1985)). This peptide has been sequenced, and has a partial beta-pleated sheet structure; hence, it is called a β-amyloid peptide or BAP.

Molecular genetic studies (primarily cDNA cloning, but also immunostaining) indicate that the β-amyloid peptide is derived from a larger amyloid precursor protein, called APP. Using a fetal brain library and an oligonucleotide probe drawn from the amino acid sequence, what appears to be a full-length cDNA clone with a 695-amino acid reading frame for the putative precursor protein has been isolated and called APP 695 (Kang, J., et al., Nature 325:733 (1987)). Other amyloid peptide precursor cDNAs with open reading frames have been subsequently isolated from other SV40-transformed libraries; a 751-amino acid putative precursor (APP 751) both from an SV40-transformed fibroblast library and a promyelocytic leukemia cell line (HL60) library (Ponte, P., et al., Nature 331:525 (1988) and Tanzi, R., et al., Nature 331:528 (1988)), and a 770-amino acid putative precursor (APP 770) from a human glioblastoma library (Kitaguchi, N., et al., Nature 331:530 (1988)). More recently, a fourth protein precursor, APP 563, was described (de Sauvage, F. and Octave, J. N., Science 245:651 (1989); it has the 208 amino acid carboxy terminal containing the BAP domain of APP 751 replaced with a novel 20-amino acid insert. These similar but nonidentical precursors probably arise through differential splicing of transcripts (Tanzi, see above; Ponte, see above; and Lemaire, H. G., et al., Nucleic Acid Res. 17:517 (1989)).

It should be noted that the APP 770 gene is constituted by 18 exons of which exons 16 and 17 encode the sequence for β-amyloid. Mutations in the APP gene have already been described. Said mutations have been reported only in exon 17.

Single base changes have been reported in exon 17 of the β-amyloid precursor protein gene (APP) in familial AD and in hereditary cerebral hemorrhage with amyloidosis Dutch type (HCHWA-D), an autosomal dominant form of cerebral amyloid angiopathy (CAA). In AD, three different amino acid substitutions were found at codon 717, while in HCHWA-D an amino acid at codon 693 was changed (Levy, E., et al., Science 248:1124 (1990); Chartier-Harlin, M. C., et al., Nature 353:844 (1991); Goate, A., et al., Nature 349:704 (1991) and Murrell, J., et al., Science 254:97 (1991)).

The present invention is based upon the finding of a mutation in exon 17 of the APP 770 gene in patients showing progressive presenile dementia and others suffering from a cerebral hemorrhage due to cerebral amyloid angiopathy.

In this family, the mutation may be responsible for the progressive deposition of β-amyloid (βA) (Glenner, G. G. and Wong, C. W., Biochem. Biophys. Res. Commun. 122:885 (1984) and Masters, C. L., et al., Proc. Natl. Acad. Sci. USA 82:4245–4249 (1985)), a 4-kDa proteolysis product of APP (Kang, J., et al., Nature 325:733 (1987)) in the blood vessel walls and in the brain parenchyma.

It is therefore an object of the present invention to provide a protein which is a raw material for producing an antibody which is useful for the diagnosis of abnormal APP processing related to the formation of amyloid plaques.

It is another object of the present invention to provide a nucleotide sequence coding for the above-mentioned protein which is useful for producing the protein by recombinant techniques.

It is still another object of the present invention to provide an antibody specific for the above-mentioned protein which is useful for the diagnosis of abnormal APP processing related to the formation of amyloid plaques.

It is a further object of the present invention to provide a DNA probe or an RNA probe useful for determining the amount of an mRNA coding for a substance causing the abnormal APP processing related to the formation of amyloid plaques in a brain cell or any cells or cell lines suitable for the study of brain metabolism for the diagnosis of the above-mentioned brain abnormality.

It is still a further object of the present invention to provide a DNA probe or an RNA probe useful for detecting a specific base sequence in a chromosomal DNA, which relates to the production of a substance involved in the formation of amyloid plaques.

It is a further object of the present invention to provide a chromosomal DNA fragment coding for mutated β-amyloid which can be used for producing a pathological model animal such as a transgenic animal for use

- in research on the deposition of β-amyloid in the blood vessel walls and in the brain parenchyma and
- in determining the relationship between the deposition of β-amyloid and presenile dementia and between β-amyloid deposition and cerebral hemorrhage due to cerebral amyloid angiopathy,
- and for the isolation of transgenic cells useful for immortalization and for drug study in presenile dementia and cerebral hemorrhage.

The invention relates to a polypeptide containing a sequence of contiguous amino acids of the polypeptide sequence coded by exon 17 of the cDNA of the APP 770 gene (e.g., APP 695, APP 751 or APP 770), with said sequence of contiguous amino acids being such that:

- it has from 5 to the total number of amino acids coded by said exon 17,
- and it contains the amino acid corresponding to codon 692 in the cDNA of the APP 770 gene and which is alanine substituted for glycine.

APP 770 gene is described in Kitaguchi et al., Nature 311:530 (1988). Exon 17 is described in Yoshikai S., et al., Gene 87:257 (1990).

The nucleotide sequence and amino acid sequence of APP 770 are deduced from Kitaguchi et al. (1988) supra and Kang, J., et al., Nature 325:733 (1986) and are represented in FIG. 4.

According to an advantageous embodiment of the invention, the polypeptide contains a sequence of contiguous amino acids of β-amyloid, with said sequence of contiguous amino acids being such that:

it contains from 5 to the total number of amino acids of β-amyloid, and it contains the amino acid corresponding to codon 692 in the cDNA of the APP 770 gene and which is alanine substituted for glycine.

The APP gene is composed of 18 exons, of which exons 16 and 17 encode the sequence for the 42 amino acids of the β-amyloid (Yoshikai, S., et al., Gene 87:257 (1990). The β-amyloid is partly inserted into the transmembrane domain with 28 amino acids protruding into the extracellular space (Kang, J., et al., Nature 325:733 (1987). The mutation described causes a substitution in the extracellular part of β-amyloid at amino acid 21, changing an alanine into a glycine (Ala→Gly). The mutation is located next to the HCHWA-D mutation which substitutes a glutamic acid for a glutamine (Glu→Gln) at amino acid 22 of β-amyloid (Levy, E., et al., Science 248:1124 (1990).

An advantageous polypeptide of the invention contains a sequence of contiguous amino acids of the APP 770 transcript, with said sequence of contiguous amino acids being such that:

it has from 5 to the total number of amino acids of APP 770 transcript, and it contains the amino acid corresponding to codon 692 in the cDNA of the APP 770 gene, and which is alanine substituted for glycine, and more particularly the following specific polypeptide:

Val-Phe-Phe-Gly-Glu-Asp-Val-Gly (SEQ ID NO:1), or a polypeptide of up to 30 amino acids containing the above-mentioned specific polypeptide.

The invention also relates to a nucleic acid sequence characterized by the fact that it codes for anyone of the polypeptides according to the invention.

The invention also relates to a nucleic acid containing a nucleotide sequence of contiguous nucleotides of exon 17, with said nucleotide sequence of contiguous nucleotides being such that:

it has from 10 to the total number of nucleotides of exon 17 from the cDNA of the APP 770 gene, and it contains the nucleotide corresponding to nucleotide position 2075 in the cDNA of the APP 770 gene (as shown in FIG. 4), and which is C substituted by G.

The invention also relates to a nucleic acid containing a nucleotide sequence of contiguous nucleotides of exons 16 and 17, with said nucleotide sequence of contiguous nucleotides being such that:

it has from 10 to the total number of nucleotides of exons 16 and 17 of the cDNA of the APP 770 gene, and it contains the nucleotide corresponding to nucleotide position 2075 in the cDNA of the APP 770 gene (as shown in FIG. 4), and which is C substituted by G.

The invention also relates to a nucleic acid containing a nucleotide sequence of contiguous nucleotides of the cDNA of the APP 770 gene, with said nucleotide sequence of contiguous nucleotides being such that:

it has from 10 to the total number of nucleotides of the cDNA of the APP 770 gene, and it contains the nucleotide corresponding to nucleotide position 2075 in the cDNA-of the APP 770 gene (as shown in FIG. 4), and which is C substituted by G, and more particularly the following oligonucleotides:
GTTCTTTGGAGAAGATG (SEQ ID NO:2)
TTCTTTGGAGAAGAT (SEQ ID NO:3), or nucleic acids containing the above-mentioned oligonucleotides.

The invention also relates to a nucleic acid containing a nucleotide sequence according to the invention inserted into a heterologous nucleic acid.

The invention also relates to a recombinant vector, particularly for cloning and/or expression, comprising a vector sequence, notably of the type plasmid, cosmid, phage DNA or virus DNA, and a recombinant nucleic acid according to the invention, in one of the nonessential sites for its replication.

The invention also relates to a recombinant vector containing in one of its nonessential sites for its replication necessary elements to promote the expression of polypeptides according to the invention in a cellular host and particularly a promoter recognized by the RNA polymerase of the cellular host, particularly an inducible promoter and possibly a sequence coding for transcription termination signals and possibly a signal sequence and/or an anchoring sequence.

The invention also relates to a recombinant vector containing the elements enabling the expression by *E. coli* of a nucleic acid according to the invention inserted in the vector, and particularly the elements enabling the expression of the gene of the invention or part thereof as a mature protein, or as part of a fusion protein containing the necessary signals for transport to the periplasmic space, with said elements possibly containing amino acid sequences to facilitate downstream processing of the protein coded by said recombinant vector.

The invention also relates to a cellular host which is transformed by a recombinant vector according to the invention, and containing the regulatory elements enabling the expression of the nucleotide sequence coding for the polypeptide of the invention in this host, as a mature protein or as part of a fusion protein, the fusion moiety of which is used in the fusion protein being a part of a non-homologous protein chosen to optimize the expression of the fusion protein, or as part of a fusion protein containing the necessary signals either for transport to the periplasmic space or for secretion in the medium of the cellular host, with said elements possibly containing amino acid sequences to facilitate downstream processing of the protein coded by said recombinant vector.

The invention also relates to a cellular host chosen from among bacteria such as E. coli, transformed by the vector according to the invention or chosen from among eukaryotic organism, transfected by a vector of the invention.

The invention also concerns an expression product of a nucleic acid expressed by a transformed cellular host according to the invention.

The invention also concerns an antibody characterized by the fact that it is directed against a recombinant polypeptide containing an epitope presenting the mutation of the invention and characterized by the fact that it does not recognize non-mutated exon 17 of the APP 770 gene (as shown in FIG. 4) at nucleotide position 2075 and which does not recognize the non-mutated APP 770 gene at nucleotide position 2075.

It should be noted that the expression "non-mutated (exon 17 or APP gene) at nucleotide position 2075" means that nucleotide position 2075 is occupied by C, which does not exclude the fact that other positions can contain mutations.

The invention also relates to nucleotide probes, hybridizing with any one of the nucleic acids of the invention or with their complementary sequences, under hybridization conditions such that they do not hybridize with the non-mutated APP 770 gene as shown in FIG. 4 (at nucleotide position 2075) or with non-mutated exon 17 (at nucleotide position 2075) or with messenger RNA of non-mutated APP 770 gene (at nucleotide position 2075) or of messenger RNA of non-mutated exon 17 (at nucleotide position 2075), and more particularly the following ones:
GTTCTTTGGAGAAGATG (SEQ ID NO:4)
TTCTTTGGAGAAGAT (SEQ ID NO:3).

The invention also relates to a process for preparing a recombinant polypeptide according to the invention comprising the following steps:
- the culture in an appropriate medium of a cellular host which has previously been transformed by an appropriate vector containing a nucleic acid of the invention, and
- the recovery of the polypeptide produced by the above-said transformed cellular host from the above-said culture.

The invention also relates to a method for the determination of the mutation at nucleotide position 2075 (with respect to the cDNA of the APP 770 gene as shown in FIG. 4) in the APP 770 gene or part of it, comprising the following steps:
- the possible previous amplification of the nucleotide sequences of the invention, liable to be contained in a biological sample taken from a patient, by means of a DNA primer set which preferably consists of oligonucleotide primers derived from the DNA sequence of the APP 770 gene,
- contacting the above-mentioned biological sample with a nucleotide probe according to the invention, under conditions enabling the production of an hybridization complex formed between said probe and said nucleotide sequence,
- detecting the above-said hybridization complex which has possibly been formed.

The biological sample can be blood lymphocytes, brain tissue, skin, subcutaneous tissue, intestine, cells from neuronal origin, meningocerebral blood vessels, hair roots, and mouth washings or extracellular cerebral deposits (amyloid plaques).

A mutation sequence can be distinguished from the corresponding wild type sequence using a variety of hybridization protocols. By way of example and not intended to be limiting, a typical protocol for the detection of a particular nucleic acid sequence bound to a solid support (e.g. a nitrocellulose membrane) is described below.

The membranes were prehybridized in a mixture containing the following components: 3×SSC (1×SSC is 0.15M NaCl plus 0.015M sodium citrate, pH 7.0), 25 mM sodium phosphate buffer (pH 7.1), 20% (v/v) deionized formamide, 0.02% Ficoll (type 400, Sigma), 0.02% bovine serum albumin, 0.02% polyvinylpyrrolidone, 0.1 mg sheared heat-denatured salmon sperm DNA ml$^{-1}$, and 0.2% SDS, usually for 0.5–1 h at the appropriate temperature. The hybridization mixture had the same composition except that approximately $10^6$ c.p.m. of $^{32}$p-labelled probe ml$^{-1}$ was added. Hybridizations were performed at the same temperature for 1–2 h. The membranes were washed for 30 min in 3×SSC, 25 mM sodium phosphate buffer (pH 7.1), 20% (v/v) deionized formamide, 0.2% SDS at the hybridization temperature.

The optimal hybridization and wash temperature is a function of several parameters such as the nature of the probe (RNA or DNA; length; %G+C; secondary structure, etc.) and the composition of the hybridization and wash solution (ionic strength, presence of hybrid-destabilizing agents, etc.).

For a probe of the invention with the following sequence: GTTCTTTGGAGAAGATG (SEQ ID NO:2), the appropriate hybridization temperature and wash temperature in the above defined medium is about 43° C.

Another method for the determination of the mutation at nucleotide position 2075 (with respect to the cDNA of the APP 770 gene as shown as in FIG. 4) in the APP 770 gene or part of it, comprises the following steps:
- the possible previous amplification of a nucleotide sequence according to the invention, liable to be contained in a biological sample taken from a patient, by means of a DNA primer set in the presence of radioactive nucleotides,
- the denaturation of the amplified nucleotide sequence to split it into two strands,
- sequencing one strand of the obtained denaturated nucleotide sequence,
- and possibly determining the sequence of said strand of nucleotide sequence containing the mutation by sequencing of the opposite strand.

This above-mentioned method, which is the direct sequencing method for the determination of the mutation in affected individuals, is described hereafter in the examples.

Another method for the determination of the mutation at nucleotide position 2075 (with respect to the cDNA of the APP 770 gene as shown in FIG. 4) in the APP 770 gene or part of it comprises the following steps:
- the amplification of a nucleotide sequence of the invention, liable to be contained in a biological sample taken from a patient, by means of a DNA primer set,
- the denaturation of the amplified nucleotide sequence to split it into two strands,
- and the separation of bands, one corresponding to the strand of the nucleotide sequence containing the mutation and the other one corresponding to the strand of the nucleotide sequence containing no mutation.

It is appropriate to carry out the same analysis on a control sample taken from an unaffected patient.

The above-mentioned method applies when the patient is heterozygous. When the patient is homozygous, it is necessary to compare the band which has been obtained with that obtained from a sample taken from an unaffected patient.

This above-mentioned method, which is the single-strand conformational analysis for the determination of the mutation in affected individuals, is described hereafter in the examples.

Another method for the determination of the mutation at nucleotide position 2075 (with respect to the cDNA of the APP 770 gene) in the APP 770 gene or part of it comprises the following steps:
- the amplification of the nucleotide sequences of the invention, liable to be contained in a biological sample taken from a patient, by means of a DNA primer set,
- the digestion with the restriction enzyme CviRI liable to cleave the CviRI site which is present in the non-mutated form and absent in the mutated form,
- the separation of the bands, resulting from the digestion, for instance on a polyacrylamide or on an agarose gel,
- the detection of the bands, for instance with ethidium bromide.

This above-mentioned method corresponds to the detection of the mutation after restriction enzyme digestion.

Another method for the determination of the mutation at nucleotide position 2075 (with respect to the cDNA of the APP 770 gene as shown in FIG. 4) in the APP 770 gene or part of it comprises the following step:

sequencing of the amino acids of the invention, with said amino acids being liable to be contained in a biological sample taken from a patient, for instance according to the method described in Prelli, F., et al., Biochem. Biophys. Res. Commun. 170:301 (1990).

It is possible to isolate amyloid fibrils from the vascular plaques or from plaques present in brain parenchyma.

A diagnostic assay to detect the presence of the mutation in amyloid fibrils (from the vascular plaques) can be the following.

Protein isolation and purification:

Leptomeningeal amyloid fibrils were isolated from patients, as previously described in Van Duinen, S. G., et al. (Proc. Natl. Acad. Sci. USA 84:5991 (1987)) and Prelli, F., et al. (Biochem. Biophys. Res. Commun. 151:1150 (1988)). Briefly, they were solubilized in 6M guanidine hydrochloride/0.1M Tris/0.17M dithiothreitol, pH 10.2, and stirred for 48 h at room temperature. After addition of 25% (v/v) of 2M guanidine hydrochloride/4M acetic acid, the solution was applied to a calibrated Sephadex G-100 column, 2.5×10 cm equilibrated with 5M guanidine hydrochloride/1M acetic acid. The purity and molecular weight of the fractions were determined on 17% polyacrylamide gels containing 0.1% sodium dodecyl sulfate (SDS) (Laemmli U.K., Nature 227:680 (1970)). Samples were pretreated with 88% formic acid for 1 h at room temperature, followed by drying under nitrogen. For Western blot analysis (Towbin, H., et al., Proc. Natl. Acad. Sci. USA 76:4350 (1979)), electrophoretic transfers of gels were carried out as previously described (Prelli, F., et al., Biochemistry 26:8251 (1987)). Polyclonal rabbit antiserum to a synthetic peptide, SP 28 (Castano, E. M., et al., Biochem. Biophys. Res. Commun. 141:782 (1986)), corresponding to the 28 $NH_2$-terminal residues of AD-vascular β-protein, was used as the first antibody, and peroxidase-conjugated goat anti-rabbit antiserum was visualized by color development with 3,3'-diaminobenzidine and hydrogen peroxide.

Enzymatic Digestion:

The amyloid protein was pretreated with 88% formic acid (Masters, C. L., et al., Proc. Natl. Acad. Sci. USA 82:4245 (1985)), dissolved in 0.2M ammonium bicarbonate, pH 8.2, and incubated (enzyme: substrate, 1:100 wt/wt) for 4 h at 37° C. with 1-tosylamido-2-phenylethyl chloromethyl ketone-treated trypsin. Proteolysis was terminated by rapid freezing followed by lyophilization.

High-Performance Liquid Chromatography (HPLC):

Tryptic peptides were isolated by reverse-phase chromatography on a μ-Bondapak $C_{18}$ column (0.78×30.0 cm, Waters) with a gradient of 0–66% acetonitrile in 0.1% (v/v) trifluoroacetic acid at pH 2.5. The column eluents were monitored at 214 nm.

Amino acid analysis:

Intact and tryptic peptides of the amyloid protein were hydrolyzed for 24 h in vacuo at 110° C. with 0.2 ml 6N HCl containing 0.01% phenol, dried, resuspended in 20 μl of methanol:water:triethylamine solution (2:2:1, v/v) and redried. Pre-column derivatization of the samples were performed by addition of 20 μl of phenylisothiocyanate: water:triethylamine:methanol (1:1:1:7, v/v). After 30 min at room temperature they were dried under vacuum and analyzed in a Waters Pico-Tag amino acid analyzer using the standard Pico-Tag method. The presence of tryptophan was determined by amino acid sequencing.

Sequence Analysis:

Sequence analysis was carried out on a 477A microsequencer and the resulting phenylthiohydantoin amino acid derivatives were identified using the online 120A PTH analyzer and the standard program (Applied Biosystems).

A diagnostic assay to detect the presence of the mutation in amyloid fibrils (from brain parenchyma) can be adapted on the protocol described in Masters, C. L. et al., Proc. Natl. Acad. Sci. USA 82:4245 (1985).

Another method for the determination of the mutation at nucleotide position 2075 (with respect to the cDNA of the APP 770 gene as shown in FIG. 4) in the APP 770 gene, or part of it, is the denaturing gradient gel electrophoresis, such as described for instance in Proc. Natl. Acad. Sci. USA, vol. 86, p. 232–236 (Jan. 1989); Genetics and Genomics, vol. 3, p. 217–223 (1988).

Another method for the determination of the mutation at nucleotide position 2075 (with respect to the cDNA of the APP 770 gene) in the APP 770 gene, or part of it, is temperature gradient gel electrophoresis (TGE) denaturation, such as described for instance in Nucleic Acids Research, vol. 15, number 13, p. 5069–5083 and p. 5085–5103 (1987).

The invention also relates to a method for producing a transgenic non-human mammalian animal (e.g., a mouse, rat, dog, guminea pig or monkey) having a probability of developing amyloid plaque deposition and/or cerebral hemorrhage. The method comprises the step of incorporating a nucleotide sequence of this invention into the genome of the non-human mammalian animal. The transgenic non-human mammalian animal can be prepared according to the protocol described in International Review of Cytology, vol. 115, p. 171–222 (1989), as well as by the method generally described in European patent application 85 304 490.

The pedigree is disguised and shows only the escapees and the patients for reasons of confidentiality. The Roman numbers left are the generations, the numbers above the symbols are the individuals. The black symbols represent affected individuals. The diagnosis of the deceased patients was made by heteroanamnesis since autopsy data was not available. The living patients were diagnosed using neurological examination, neuropsychological testing and brain imaging techniques. Individuals III-4, III-11, IV-1 and IV-3 are patients who suffered a cerebral hemorrhage; all other patients are patients with probable Alzheimer's disease. The presence (+) or absence (−) of the mutation as determined by direct sequencing or SSCA as well as the alleles of the 21-GT12 (D21S210) marker are indicated below the symbols.

FIG. 2: Biopsy of patient IV-3.

A, Senile plaques;

B, congophilic angiopathy stained with the polyclonal antiserum β-amyloid 1–42 (Masters, C. L., et al., Proc. Natl. Acad. Sci. USA 82:4245 (1985));

C, Dystrophic senile plaque neurites were labelled with an ubiquitin polyclonal antiserum (Perry, G., et al., Proc. Natl. Acad. Sci. USA 84:3033 (1987));

D, In a semi-serial section, these neurites were negative with AT8, a monoclonal antibody directed against abnormally phosphorylated tau filed at ECACC on Oct. 8, 1991 under No. 91100806.

Methods. Unlabelled antibody bridge or avidin-biotin-labelled immunoperoxidase techniques were used with diaminobenzidine as substrate. The sections were counterstained with hematoxylin.

FIG. 3:

a, Autoradiography of the sequencing gel from part of the APP 770 exon 17 in individual IV-3 (FIG. 1) and in an unaffected family member showing a single base pair change at position 2075. The C to G transversion leads to an amino acid substitution of an Ala into a Gly at codon 692 of the APP 770 transcript (Yoshikai et al., see supra).

Figure 1:
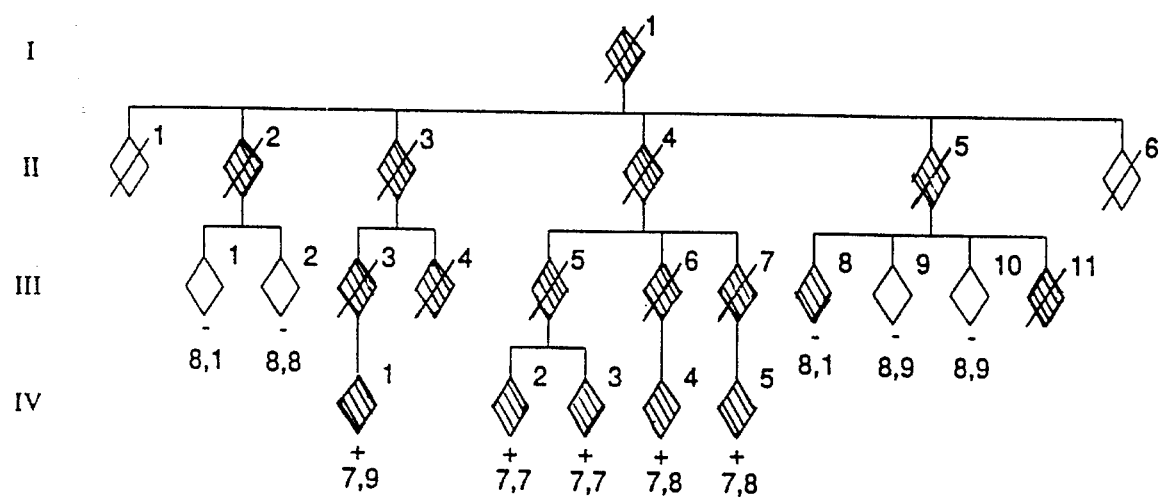
FIG. 1: Family 1302.

Methods. The conditions and the primers for the PCR amplification of exon 17 were as described (Bakker, E., et al., Am. J. Hum. Genet. 49:518 (1991)). In the amplification, a biotinylated 3' primer was used and the PCR product was bound to streptavidin-coated magnetic beads (Dynal). After DNA denaturation the single-stranded DNA was sequenced (Uhlen, M., Nature 340:733 (1989)) using the Sequenase kit version 2.0 (USB) and the 5' primer. The presence of the mutation was confirmed after sequencing of the opposite strand (data not shown).

b, Single-strand conformational analysis (SSCA) of the mutation at codon 692 in one normal and 6 affected individuals from family 1302 showing the presence of the mutation in all affected, with the exception of one, individual III-8. The numbers refer to the generation number of the individual in the pedigree (FIG. 1).

Methods. The amplification of exon 17 was performed (Bakker et al., see supra) in the presence of [β-$^{32}$P]dCTP. After denaturation, the PCR product was loaded on a 5% non-denaturing polyacrylamide gel containing 10% glycerol (Orita, M., et al., Genomics 5:874 (1989)).

FIG. 4:

DNA sequence and encoded amino acid sequence of the APP 770 cDNA according to Kitaguchi et al., Nature 311:530 (1988) and Kang et al., Nature 325:733 (1986). Nucleotide position numbers are indicated above the DNA sequence.

EXAMPLE 1:

Identification of the codon 692 mutation in the APP 770 gene

In an epidemiological study of genetic risk factors in Alzheimer's disease (Hofman, A., et al., Neurology 39:1589 (1989)), a four-generation family, coded 1302, was identified with autosomal dominant presenile dementia fulfilling the NINCDS criteria (McKhann, G., et al., Neurology 34:939 (1984)) for probable AD (FIG. 1). The mean age at onset of dementia was 49.3±6.7 years (n=7, range 41 to 61 years) and the mean age at death 57.7±6.5 years (n=9, range 47 to 68 years). In the family, were also identified 4 patients with a cerebral hemorrhage at a mean age of 39.5±3.1 years (range 35 to 42 years). Prior to the cerebral hemorrhage these patients did not show signs of dementia. Family 1302 was not related to the known HCHWA-D families.

Figures 2A, 2B, 2C, 2D:
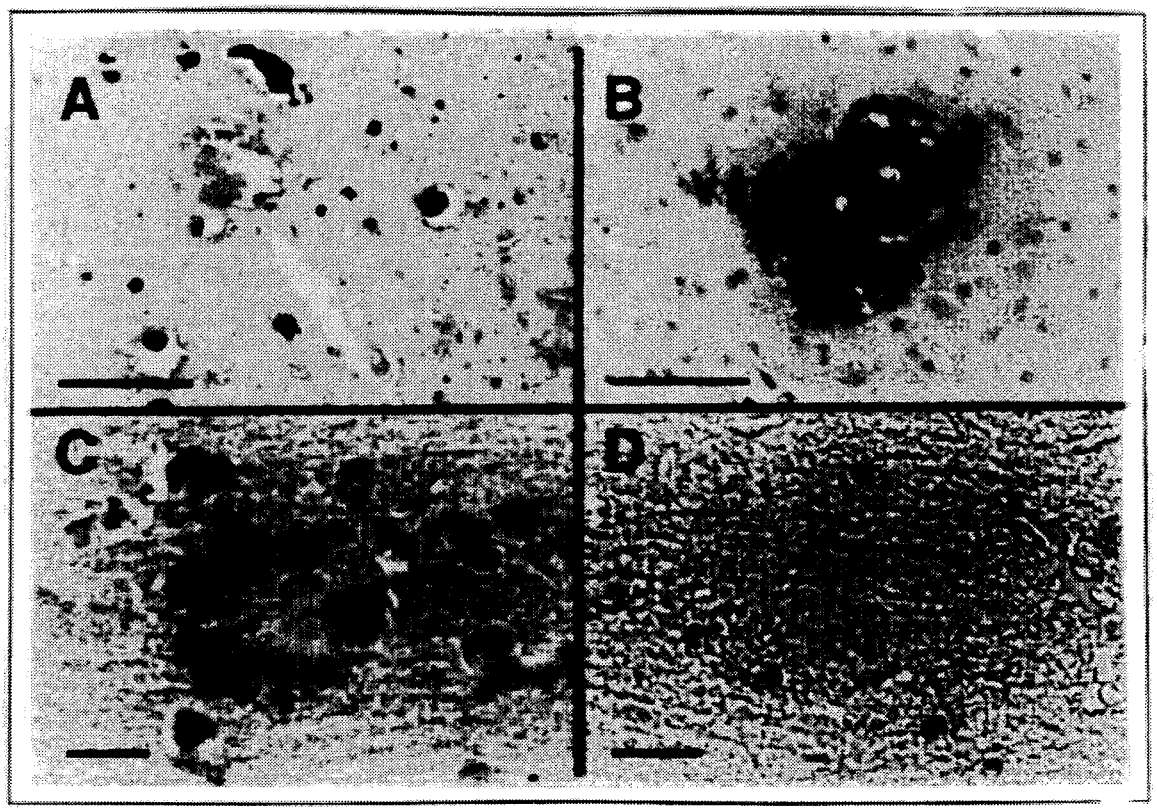

One patient (IV-3 in FIG. 1) who suffered from a large hemorrhage in the left parieto-occipital cortex was studied in more detail. The hematoma was evacuated and biopsies were taken. Immunohistochemistry on the biopsy material with a β-amyloid polyclonal antiserum, showed extensive amyloid deposition in the blood vessel walls and in parenchymal senile plaques (FIG. 2A and 2B). The senile plaques were predominantly diffuse amyloid deposits but neuritic plaques with a dense amyloid core were also observed. Dystrophic neurites in the senile plaques and in the perivascular amyloid depositions were immunostained by a polyclonal antiserum to ubiquitin (FIG. 2C). However, no neurofibrillary tangles were detected using a monoclonal antibody to pathological tau (FIG. 2D).

Figure 3A:
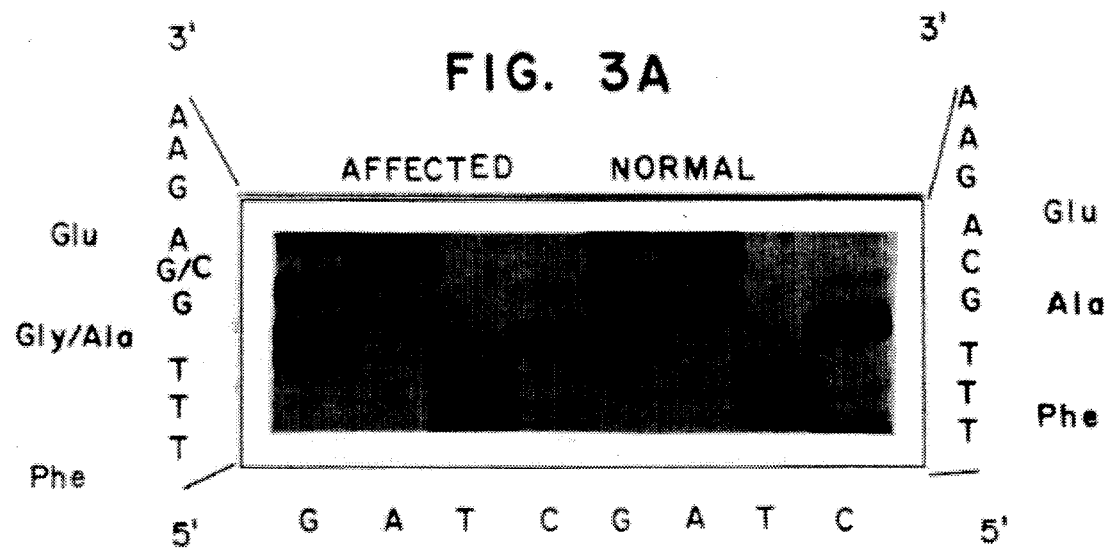
Figure 3B:
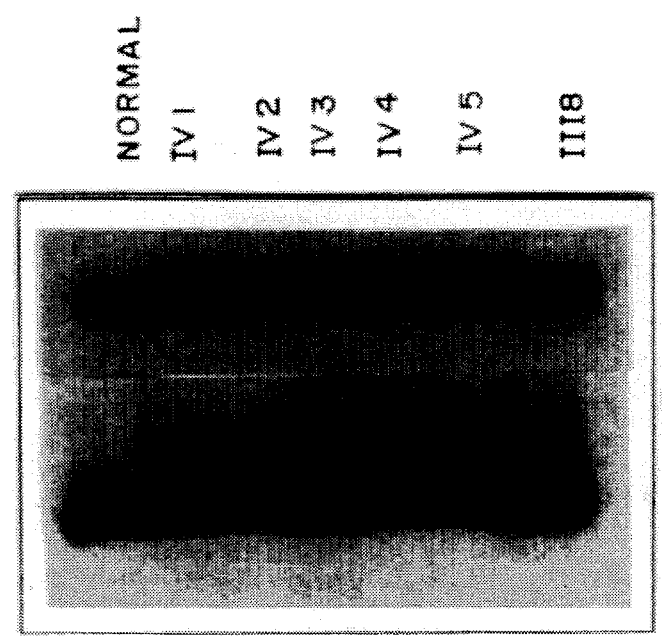

The possible presence of a mutation in exon 17 of the APP gene in patient IV-3 was examined. Leukocyte DNA was used for PCR amplification and direct sequencing (FIG. 3a). Neither the HCHWA-D mutation nor the known AD mutations were found. Instead, a novel C-to-G transversion at position 2075 substituting alanine (Ala) into glycine (Gly) at codon 692 of the APP 770 transcript (Yoshikai, S., et al., Gene 87:257 (1990)) was detected. Direct sequencing and single-strand conformational analysis (SSCA) were used to test for the mutation in the affected individuals. Theoretically the mutation can also be detected after restriction enzyme digestion since the C-to-G transversion destroys a CviRI recognition site. The mutation was present in patient IV-1 with cerebral hemorrhage and in patients IV-2, IV-4, and IV-5, but not in patient III-8, with dementia (FIG. 3b). In the latter patient, the onset at 61 years occurred considerably later than the mean age of onset (47.3±4.6 years, n=6, range 41 to 55 years) found in the other relatives with dementia, and the current age of 71 years is outside the range of the age at death. Therefore, it is thought likely that the dementia in this patient has a different etiology.

The presence of the mutation in the unaffected individuals by SSCA was also tested. In generation III (FIG. 1), the mutation was absent in III-1, III-2, III-9, and III-10, all individuals who, on the basis of their ages ranging from 64 to 76 years, were judged to have escaped the disease. In generation IV, the age of the 7 unaffected individuals ranged from 38 to 59 years. The mutation was present in 2 of them (individuals not shown for reasons of confidentiality). Possible applications of the mutation in presymptomatic testing are under study, also since in the 2 unaffected individuals carrying the mutation, and currently aged 41 years, suggestive symptoms are starting to occur.

Segregation analysis with the highly polymorphic dinucleotide repeat marker 21-GT12 (D21S210) located close to the APP 770 gene, showed that the mutation segregated with allele 7 (FIG. 1). Allele 7 is not present in individual III-8 indicating that in this patient the dementia recombines with the 21-GT12 marker. The recombination was also observed with the BglII polymorphism detected by the β-amyloid fragment of the APP 770 cDNA (Van Broeckhoven, C., et al., Nature 329:153 (1987)) (data not shown). Linkage was calculated and included all individuals analyzed, except individual III-8. The peak lod score of 2.32 for the 21-GT12 marker and of 3.45 for the mutation at a recombination fraction, Θ, of zero (Table 1 below), confirmed that the 21-GT12 marker and the mutation cosegregate with the disease. Further, SSCA showed that the mutation did not occur in 100 normal, unrelated Caucasians.

Table 1 hereafter shows the lod scores for linkage.

TABLE 1

| | Recombination fraction Θ | | | | | | |
|---|---|---|---|---|---|---|---|
| | 0.0 | 0.01 | 0.05 | 0.10 | 0.20 | 0.30 | 0.40 |
| APP 692 | 3.45 | 3.38 | 3.09 | 2.73 | 2.02 | 1.30 | 0.57 |
| 21-GT12 | 2.32 | 2.26 | 2.00 | 1.68 | 1.11 | 0.58 | 0.14 |

Table 1

The lod scores were calculated using the MLINK from the LINKAGE package (Lathrop, G., et al., Proc. Natl. Acad. Sci. USA 81:3443 (1984)) assuming a disease frequency of 0.001 and a phenocopy rate of 0.001. The penetrance for the unaffected individuals was estimated from an age at onset curve (Ott, J. in Analysis of Human Genetic Linkage; The Johns Hopkins University Press (eds. Boyer, S. H. et al.) 141–144 (1985)), using a mean age at onset of 44.8±3.3 years calculated in the 5 living patients in generation IV (FIG. 1). The frequency for the APP 692 mutation was 0.01. The allele frequencies of 21-GT12 (D21S210) are available from the Genome Data Base (GDB).

The results obtained suggest that in family 1302 both probable Alzheimer's disease and cerebral hemorrhage are linked to the same mutation at codon 692 of the APP 770 gene. It remains, however, possible that other sequence differences exist in the APP 770 gene since other exons or the promotor sequence in the patients have not yet been analyzed. Nonetheless, mutations other than in exon 17 have not been reported yet.

In the biopsy of patient IV-3, the distribution and quantity of β-amyloid deposits is similar to that seen in HCHWA-D patients (Timmers, W. F., et al., Neurosci. Lett. 118:223 (1990)). Dystrophic neurites were present but no neurofibrillary tangles were observed. However, since autopsy data are not available, the possibility that neurofibrillary tangles will develop as the amyloid deposition progresses cannot be excluded. Normally β-amyloid deposition is prevented since the APP is cleaved within the β-amyloid fragment at amino acid 16 by the APP secretase (Sisodia, S. S., et al. Science 248:492 (1990) and Esch, F. S., et al., Science 248:1122 (1990)). The mutation in family 1302 and in HCHWA-D may alter the efficiency of the APP secretase allowing the processing of APP through alternative pathways that leave the β-amyloid fragment intact. In HCHWA-D families the common clinical manifestation is a cerebral hemorrhage due to extensive cerebral amyloid angiopathy (Haan, J., et al., Arch. Neurol. 47:965 (1990)). In most HCHWA-D patients surviving one or more hemorrhages, dementia was recorded, and some patients showed progressive dementia in the absence of apparent cerebral hemorrhage (Haan, J., et al., Arch. Neurol. 47:649 (1990)). In family 1302, most patients demonstrate dementia in the absence of cerebral hemorrhage.

EXAMPLE 2:

Introduction of the codon 692 mutation into the APP 770 and APP 695 cDNAs

The mutation at amino acid position 692 of the APP 770 (nucleotide position 2075: C to G) is introduced in the human APP 770 and APP 695 cDNA sequences (Kang et al (1987) supra). Human APP cDNA is cloned in the plasmid pcDNAO/neo (Invitrogen, Abingdon, UK). Since this vector has a low copy number and is difficult to use, the APP cDNA is subcloned in the HindIII restriction site of a modified pSG5 vector (Stratagene, La Jolla, Calif., USA), provided by Prof. F. Van Leuven, Centrum voor Menselijke Erfelykheid, K. U. Leuven, Belgium. The modified vector, pSG5**, has extra unique cloning sites as compared with the original pSG5 vector.

The APP-pSG5** construct is used for site-directed mutagenesis by the method of Deng and Nickoloff, Anal. Biochem. 200: 81–88 (1992). The method works by simultaneously annealing two oligonucleotide primers to one strand of a recombinant plasmid. The mutagenic primer introduces the desired mutation, and the selection primer creates or abolishes a unique restriction enzyme site of the recombinant plasmid.

Oligonucleotide primers

Two oligonucleotide primers are synthesized: 1) the mutagenic primer comprising the C to G substitution at nucleotide position 2075 (in APP 770 as shown in FIG. 4), and 2) the selection primer which is complementary to the vectoral sequence and destroys a unique NotI restriction site for the construct (see below). The primers are purified on OPC columns (Applied Biosystems, Foster City, Calif., USA).

1 μg (110 pmol for 27-mer) of each primer is phosphorilated in the presence of 50 mM Tris-HCl (pH 7.5), 10 mM MgCl$_2$, 5 mM DTT, 1 mM ATP and 10 U polynucleotide kinase (New England Biolabs, Beverly, Mass., USA) at 37° C. for 1 hour. The enzyme activity is stopped by placing the tube for 10 min. at 65° C.

1) Mutagenic primer introducing the 692 codon mutation in APP:

(SEQ ID NO: 5)
TTG GTT TTC TTT GGA GAA GAT GTG GGT

2) Selection primer abolishing a unique NotI restriction site in the APP-pSG5** construct:

(SEQ ID NO: 6)
AAG CTT GCG GCC ACA CTC GAG CCC GGG

These primer sequences are used for in vitro mutagenesis of the APP 695 and 770 cDNAs. The underlined nucleotide is the mutated one in each primer.

Site-directed mutagenesis

Site-directed mutagenesis is carried out using a kit of Clontech (Palo Alto, Calif., USA). 100 ng of the mutagenic primer and 100 ng of the selection primer are annealed to 100 ng of each of the target plasmids (human APP 695 and human APP 770 cloned in pSG5**), in the presence of 20 mM Tris-HCl (pH 7.5), 10 mM MgCl$_2$, 50 mM Nacl, by boiling the mixture for 3 minutes and subsequently cooling on ice for 5 min. The synthesis of the mutant DNA is performed in 1x synthese buffer (nucleotides in optimum concentration), 2–4 U T4 DNA polymerase, 4–6 U T4 DNA ligase at 37° C. for 2 hours. The reaction is stopped by adding 1/10th volume 0.25% SDS and 50 mM EDTA (pH 8.0) and incubating the mix for 10 min at 65° C.

Approximately 1/150th of this mixture (0.66 nm target plasmid) is used for transformation in electrocompetent E. coli BMH 71-18 mutS cells (Clontech). Electroporation is done at 2.5 kV in a 0.2 cm cuvette with an E. coli pulser (BioRad, Richmond, Calif., USA). Immediately after the pulse, 1 ml SOC medium (2% Bactotryptone, 0.5% yeast extract, 10 mM NaCl, 2.5 KCl, 10 mM MgCl$_2$, 20 mM glucose) is added, and cells are allowed to recover for 1 hour at 37° C. The 10 ml LB-medium (1% Bactotryptone, 0.5% yeast extract, 17 mM NaCl) with 50 μg/ml ampicillin is added, and the culture is incubated overnight at 37° C., shaking. Plasmid preparation is done by the alkaline lysis method (Birnboim and Doly, Nucl. Acids Res. 7: 1513–1523 (1979)) using Qiagen (Hilden, Germany) columns. In order to enrich the mutated clones, a NotI digest is performed on 0.5 μg plasmid. After a 1 hour digestion, approximately 100 ng of plasmid is transformed in competent E. coli Dh5 alpha cells by chemical transformation (Cohen et al, Proc. Natl. Acad. Sci. USA 69:2110 (1972)). The cells are plated on LB plates containing 50 μg/ml ampicillin.

For each target clone, 10 colonies are picked up, and plasmid DNA is prepared and digested with NotI. Clones which do not cut with NotI are selected and sequenced to confirm the presence of the 692 codon mutation.

Applications

Cell cultures

First, the mutated APP 770 and APP 695 cDNAs cloned in the modified pSG5** vector are directly used in COS cell transfections experiments in which the mutated APP 770 and 695 cDNAs are expressed. Also, transfection in neuroblastoma cell lines is performed, and intracellular and excreted expression products of the mutated APP 770 and 695 cDNAs are obtained.

Transgenic mice

In order to create transgenic mice, each of the mutated APP 770 and 695 cDNAs is isolated from the modified pSG5** vector with a SpeI digest and cloned in a different vector containing an enhancer, the human APP promoter, a Beta-globin intron and a poly A signal provided by Prof. Van Leuven. After amplification of each vector, the viral and bacterial sequences are removed and injected into mouse oocytes. Offspring are tested and each found to contain the mutated human APP 770 or 695 cDNA, and such offspring are then subjected to pathological and behavioral tests showing their usefulness as test animals.

We claim:

1. An isolated nucleic acid consisting of a nucleotide sequence of contiguous nucleotides of exon 17, wherein said nucleotide sequence:
   has the total number of nucleotides of exon 17 of the cDNA of the APP 770 gene;
   and contains the nucleotide which corresponds to nucleotide position 2075 in the cDNA of the APP 770 gene wherein C is substituted by G of sequence I.D. No. 7.

2. An isolated nucleic acid consisting of a nucleotide sequence of contiguous nucleotides of exons 16 and 17, wherein said nucleotide sequence:
   has the total number of nucleotides of exons 16 and 17 of the cDNA of the APP 770 gene;
   and contains the nucleotide which corresponds to nucleotide position 2075 in the cDNA of the APP 770 gene wherein C is substituted by G of Sequence I.D. No. 7.

3. An isolated nucleic acid comprising a nucleotide sequence of contiguous nucleotides of the cDNA of the APP 770 gene, wherein said nucleotide sequence:
   has the total number of nucleotides of the cDNA of the APP 770 gene;
   and contains the nucleotide corresponding to nucleotide position 2075 in the cDNA of the APP 770 gene, wherein C is substituted by G of Sequence I.D. No. 7.

4. An isolated nucleic sequence encoding a polypeptide consisting of a sequence of contiguous amino acids of the polypeptide sequence coded by exon 17 of the cDNA of the APP 770 gene wherein said contiguous amino acid sequence has the total number of amino acids encoded by exon 17 and contains the amino acid corresponding to codon 692 in the cDNA of the APP 770 gene wherein alanine is substituted by glycine of Sequence I.D. No. 8.

5. An isolated nucleic acid sequence encoding a polypeptide consisting of a sequence of contiguous amino acids of β-amyloid, said contiguous amino acid sequence containing the total number of amino acids of β-amyloid and an amino acid corresponding to codon 692 in the cDNA of the APP 770 gene wherein alanine is substituted by glycine of Sequence I.D. No. 8.

6. An isolated nucleic acid sequence encoding a sequence of contiguous amino acids of an APP 770 transcript, wherein said contiguous amino acid sequence has the total number of amino acids of the APP 770 transcript and contains the amino acid corresponding to codon 692 in the cDNA of the APP 770 gene wherein alanine is substituted by glycine.

7. The nucleic acid sequence according to claim 6, wherein said contiguous amino acid sequence is:

Val — Phe — Phe — Gly — Glu — Asp — Val — Gly.    SEQ ID No. 1

8. The nucleic acid sequence according to claim 3, wherein said contiguous nucleic acid sequence is:

GTTCTTTGGAGAAGATG    SEQ ID No. 2

TTCTTTGGAAAGAT.    SEQ ID No. 3

9. An isolated nucleic acid consisting of a nucleotide sequence according to claim 4 inserted into a recombinant nucleic acid vector.

10. A recombinant vector, comprising a vector sequence, such as a plasmid, a phage DNA or a virus DNA, and an isolated nucleic acid according to claim 4.

11. A recombinant vector according to claim 10, containing elements to promote the expression of said isolated nucleic acid.

12. A recombinant vector according to claim 11, containing the elements enabling the expression by E. coli with said elements containing amino acid sequences to facilitate downstream processing and transport to the periplasmic space of the protein coded by said recombinant vector.

13. A cellular host transformed by a recombinant vector according to claim 11, and containing the regulation elements enabling the expression of a nucleotide sequence.

14. A cellular host according to claim 13, wherein said cellular host is E. coli.

15. The recombinant vector according to claim 11, wherein said vector further comprises a promoter recognized by the RNA polymerase of the cellular host, a sequence coding for transcription termination signals and a signal sequence or an anchoring sequence.

16. The recombinant vector according to claim 15, wherein said promoter is an inducible promoter.

17. The recombinant vector according to claim 11, wherein said cellular host is an eukaryotic microorganism.

18. A recombinant vector comprising a plasmid, a cosmid, a phage DNA or a virus DNA and a nucleic acid sequence of claim 5.

19. A recombinant vector comprising a plasmid, a cosmid, a phage DNA or a virus DNA and a nucleic acid sequence of claim 6.

20. The recombinant vector according to claim 11, wherein said vector further comprises a promoter recognized by the RNA polymerase of the cellular host, a sequence coding for transcription termination signals and a signal sequence and an anchoring sequence.

* * * * *

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
      ( A ) LENGTH: 8 amino acids
      ( B ) TYPE: amino acid
      ( D ) TOPOLOGY: linear ( i i ) MOLECULE TYPE: peptide ( x i ) SEQUENCE DESCRIPTION: SEQ ID NO: 1:

```
Val  Phe  Phe  Gly  Glu  Asp  Val  Gly
 1                    5
```

( 2 ) INFORMATION FOR SEQ ID NO: 2:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO: 2:

```
GTTCTTTGGA GAAGATG                                                         17
```

( 2 ) INFORMATION FOR SEQ ID NO: 3:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO: 3:

```
TTCTTTGGAG AAGAT                                                           15
```

( 2 ) INFORMATION FOR SEQ ID NO: 4:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO: 4:

GTTCTTTGGA GAAGATG     17

( 2 ) INFORMATION FOR SEQ ID NO: 5:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO: 5:

TTGGTGTTCT TTGGAGAAGA TGTGGGT     27

( 2 ) INFORMATION FOR SEQ ID NO: 6:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO: 6:

AAGCTTGCGG CCACACTCGA GCCCGGG     27

( 2 ) INFORMATION FOR SEQ ID NO: 7:

( i ) SEQUENCE CHARACTERISTICS:
        ( A ) LENGTH: 2313 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i i i ) ANTI-SENSE: NO ( i x ) FEATURE:
        ( A ) NAME/KEY: CDS
        ( B ) LOCATION: 1..2313

( i x ) FEATURE:
        ( A ) NAME/KEY: mat_peptide
        ( B ) LOCATION: 1..2310

( x i ) SEQUENCE DESCRIPTION: SEQ ID NO: 7:

```
ATG  CTG  CCC  GGT  TTG  GCA  CTG  CTC  CTG  CTG  GCC  GCC  TGG  ACG  GCT  CGG      48
Met  Leu  Pro  Gly  Leu  Ala  Leu  Leu  Leu  Leu  Ala  Ala  Trp  Thr  Ala  Arg
 1                  5                       10                      15

GCG  CTG  GAG  GTA  CCC  ACT  GAT  GGT  AAT  GCT  GGC  CTG  CTG  GCT  GAA  CCC      96
Ala  Leu  Glu  Val  Pro  Thr  Asp  Gly  Asn  Ala  Gly  Leu  Leu  Ala  Glu  Pro
             20                      25                      30
```

| | | | | | | | | | | | | | | | | |
|---|---|---|---|---|---|---|---|---|---|---|---|---|---|---|---|---|
| CAG | ATT | GCC | ATG | TTC | TGT | GGC | AGA | CTG | AAC | ATG | CAC | ATG | AAT | GTC | CAG | 144 |
| Gln | Ile | Ala | Met | Phe | Cys | Gly | Arg | Leu | Asn | Met | His | Met | Asn | Val | Gln | |
| | | 35 | | | | | 40 | | | | | 45 | | | | |
| AAT | GGG | AAG | TGG | GAT | TCA | GAT | CCA | TCA | GGG | ACC | AAA | ACC | TGC | ATT | GAT | 192 |
| Asn | Gly | Lys | Trp | Asp | Ser | Asp | Pro | Ser | Gly | Thr | Lys | Thr | Cys | Ile | Asp | |
| | 50 | | | | | 55 | | | | | 60 | | | | | |
| ACC | AAG | GAA | GGC | ATC | CTG | CAG | TAT | TGC | CAA | GAA | GTC | TAC | CCT | GAA | CTG | 240 |
| Thr | Lys | Glu | Gly | Ile | Leu | Gln | Tyr | Cys | Gln | Glu | Val | Tyr | Pro | Glu | Leu | |
| 65 | | | | | 70 | | | | | 75 | | | | | 80 | |
| CAG | ATC | ACC | AAT | GTG | GTA | GAA | GCC | AAC | CAA | CCA | GTG | ACC | ATC | CAG | AAC | 288 |
| Gln | Ile | Thr | Asn | Val | Val | Glu | Ala | Asn | Gln | Pro | Val | Thr | Ile | Gln | Asn | |
| | | | | 85 | | | | | 90 | | | | | 95 | | |
| TGG | TGC | AAG | CGG | GGC | CGC | AAG | CAG | TGC | AAG | ACC | CAT | CCC | CAC | TTT | GTG | 336 |
| Trp | Cys | Lys | Arg | Gly | Arg | Lys | Gln | Cys | Lys | Thr | His | Pro | His | Phe | Val | |
| | | | 100 | | | | | 105 | | | | | 110 | | | |
| ATT | CCC | TAC | CGC | TGC | TTA | GTT | GGT | GAG | TTT | GTA | AGT | GAT | GCC | CTT | CTC | 384 |
| Ile | Pro | Tyr | Arg | Cys | Leu | Val | Gly | Glu | Phe | Val | Ser | Asp | Ala | Leu | Leu | |
| | | | 115 | | | | | 120 | | | | | 125 | | | |
| GTT | CCT | GAC | AAG | TGC | AAA | TTC | TTA | CAC | CAG | GAG | AGG | ATG | GAT | GTT | TGC | 432 |
| Val | Pro | Asp | Lys | Cys | Lys | Phe | Leu | His | Gln | Glu | Arg | Met | Asp | Val | Cys | |
| | | 130 | | | | | 135 | | | | | 140 | | | | |
| GAA | ACT | CAT | CTT | CAC | TGG | CAC | ACC | GTC | GCC | AAA | GAG | ACA | TGC | AGT | GAG | 480 |
| Glu | Thr | His | Leu | His | Trp | His | Thr | Val | Ala | Lys | Glu | Thr | Cys | Ser | Glu | |
| 145 | | | | | 150 | | | | | 155 | | | | | 160 | |
| AAG | AGT | ACC | AAC | TTG | CAT | GAC | TAC | GGC | ATG | TTG | CTG | CCC | TGC | GGA | ATT | 528 |
| Lys | Ser | Thr | Asn | Leu | His | Asp | Tyr | Gly | Met | Leu | Leu | Pro | Cys | Gly | Ile | |
| | | | | 165 | | | | | 170 | | | | | 175 | | |
| GAC | AAG | TTC | CGA | GGG | GTA | GAG | TTT | GTG | TGT | TGC | CCA | CTG | GCT | GAA | GAA | 576 |
| Asp | Lys | Phe | Arg | Gly | Val | Glu | Phe | Val | Cys | Cys | Pro | Leu | Ala | Glu | Glu | |
| | | | 180 | | | | | 185 | | | | | 190 | | | |
| AGT | GAC | AAT | GTG | GAT | TCT | GCT | GAT | GCG | GAG | GAG | GAT | GAC | TCG | GAT | GTC | 624 |
| Ser | Asp | Asn | Val | Asp | Ser | Ala | Asp | Ala | Glu | Glu | Asp | Asp | Ser | Asp | Val | |
| | | 195 | | | | | 200 | | | | | 205 | | | | |
| TGG | TGG | GGC | GGA | GCA | GAC | ACA | GAC | TAT | GCA | GAT | GGG | AGT | GAA | GAC | AAA | 672 |
| Trp | Trp | Gly | Gly | Ala | Asp | Thr | Asp | Tyr | Ala | Asp | Gly | Ser | Glu | Asp | Lys | |
| | 210 | | | | | 215 | | | | | 220 | | | | | |
| GTA | GTA | GAA | GTA | GCA | GAG | GAG | GAA | GAA | GTG | GCT | GAG | GTG | GAA | GAA | GAA | 720 |
| Val | Val | Glu | Val | Ala | Glu | Glu | Glu | Glu | Val | Ala | Glu | Val | Glu | Glu | Glu | |
| 225 | | | | | 230 | | | | | 235 | | | | | 240 | |
| GAA | GCC | GAT | GAT | GAC | GAG | GAC | GAT | GAG | GAT | GGT | GAT | GAG | GTA | GAG | GAA | 768 |
| Glu | Ala | Asp | Asp | Asp | Glu | Asp | Asp | Glu | Asp | Gly | Asp | Glu | Val | Glu | Glu | |
| | | | | 245 | | | | | 250 | | | | | 255 | | |
| GAG | GCT | GAG | GAA | CCC | TAC | GAA | GAA | GCC | ACA | GAG | AGA | ACC | ACC | AGC | ATT | 816 |
| Glu | Ala | Glu | Glu | Pro | Tyr | Glu | Glu | Ala | Thr | Glu | Arg | Thr | Thr | Ser | Ile | |
| | | | 260 | | | | | 265 | | | | | 270 | | | |
| GCC | ACC | ACC | ACC | ACC | ACC | ACC | ACA | GAG | TCT | GTG | GAA | GAG | GTG | GTT | CGA | 864 |
| Ala | Thr | Thr | Thr | Thr | Thr | Thr | Thr | Glu | Ser | Val | Glu | Glu | Val | Val | Arg | |
| | | 275 | | | | | 280 | | | | | 285 | | | | |
| GAG | GTG | TGC | TCT | GAA | CAA | GCC | GAG | ACG | GGG | CCG | TGC | CGA | GCA | ATG | ATC | 912 |
| Glu | Val | Cys | Ser | Glu | Gln | Ala | Glu | Thr | Gly | Pro | Cys | Arg | Ala | Met | Ile | |
| | | 290 | | | | | 295 | | | | | 300 | | | | |
| TCC | CGC | TGG | TAC | TTT | GAT | GTG | ACT | GAA | GGG | AAG | TGT | GCC | CCA | TTC | TTT | 960 |
| Ser | Arg | Trp | Tyr | Phe | Asp | Val | Thr | Glu | Gly | Lys | Cys | Ala | Pro | Phe | Phe | |
| 305 | | | | | 310 | | | | | 315 | | | | | 320 | |
| TAC | GGC | GGA | TGT | GGC | GGC | AAC | CGG | AAC | AAC | TTT | GAC | ACA | GAA | GAG | TAC | 1008 |
| Tyr | Gly | Gly | Cys | Gly | Gly | Asn | Arg | Asn | Asn | Phe | Asp | Thr | Glu | Glu | Tyr | |
| | | | 325 | | | | | 330 | | | | | 335 | | | |
| TGC | ATG | GCC | GTG | TGT | GGC | AGC | GCC | ATG | TCC | CAA | AGT | TTA | CTC | AAG | ACT | 1056 |
| Cys | Met | Ala | Val | Cys | Gly | Ser | Ala | Met | Ser | Gln | Ser | Leu | Leu | Lys | Thr | |
| | | | 340 | | | | | 345 | | | | | 350 | | | |

| | | | | | | | | | | | | | | | | |
|---|---|---|---|---|---|---|---|---|---|---|---|---|---|---|---|---|
| ACC | CAG | GAA | CCT | CTT | GCC | CGA | GAT | CCT | GTT | AAA | CTT | CCT | ACA | ACA | GCA | 1104 |
| Thr | Gln | Glu | Pro | Leu | Ala | Arg | Asp | Pro | Val | Lys | Leu | Pro | Thr | Thr | Ala | |
| | 355 | | | | | 360 | | | | | 365 | | | | | |
| GCC | AGT | ACC | CCT | GAT | GCC | GTT | GAC | AAG | TAT | CTC | GAG | ACA | CCT | GGG | GAT | 1152 |
| Ala | Ser | Thr | Pro | Asp | Ala | Val | Asp | Lys | Tyr | Leu | Glu | Thr | Pro | Gly | Asp | |
| 370 | | | | | 375 | | | | | 380 | | | | | | |
| GAG | AAT | GAA | CAT | GCC | CAT | TTC | CAG | AAA | GCC | AAA | GAG | AGG | CTT | GAG | GCC | 1200 |
| Glu | Asn | Glu | His | Ala | His | Phe | Gln | Lys | Ala | Lys | Glu | Arg | Leu | Glu | Ala | |
| 385 | | | | 390 | | | | | 395 | | | | | | 400 | |
| AAG | CAC | CGA | GAG | AGA | ATG | TCC | CAG | GTC | ATG | AGA | GAA | TGG | GAA | GAG | GCA | 1248 |
| Lys | His | Arg | Glu | Arg | Met | Ser | Gln | Val | Met | Arg | Glu | Trp | Glu | Glu | Ala | |
| | | | | 405 | | | | | 410 | | | | | 415 | | |
| GAA | CGT | CAA | GCA | AAG | AAC | TTG | CCT | AAA | GCT | GAT | AAG | AAG | GCA | GTT | ATC | 1296 |
| Glu | Arg | Gln | Ala | Lys | Asn | Leu | Pro | Lys | Ala | Asp | Lys | Lys | Ala | Val | Ile | |
| | | | 420 | | | | | 425 | | | | | 430 | | | |
| CAG | CAT | TTC | CAG | GAG | AAA | GTG | GAA | TCT | TTG | GAA | CAG | GAA | GCA | GCC | AAC | 1344 |
| Gln | His | Phe | Gln | Glu | Lys | Val | Glu | Ser | Leu | Glu | Gln | Glu | Ala | Ala | Asn | |
| | | 435 | | | | | 440 | | | | | 445 | | | | |
| GAG | AGA | CAG | CAG | CTG | GTG | GAG | ACA | CAC | ATG | GCC | AGA | GTG | GAA | GCC | ATG | 1392 |
| Glu | Arg | Gln | Gln | Leu | Val | Glu | Thr | His | Met | Ala | Arg | Val | Glu | Ala | Met | |
| | 450 | | | | | 455 | | | | | 460 | | | | | |
| CTC | AAT | GAC | CGC | CGC | CGC | CTG | GCC | CTG | GAG | AAC | TAC | ATC | ACC | GCT | CTG | 1440 |
| Leu | Asn | Asp | Arg | Arg | Arg | Leu | Ala | Leu | Glu | Asn | Tyr | Ile | Thr | Ala | Leu | |
| 465 | | | | | 470 | | | | | 475 | | | | | 480 | |
| CAG | GCT | GTT | CCT | CCT | CGG | CCT | CGT | CAC | GTG | TTC | AAT | ATG | CTA | AAG | AAG | 1488 |
| Gln | Ala | Val | Pro | Pro | Arg | Pro | Arg | His | Val | Phe | Asn | Met | Leu | Lys | Lys | |
| | | | | 485 | | | | | 490 | | | | | 495 | | |
| TAT | GTC | CGC | GCA | GAA | CAG | AAG | GAC | AGA | CAG | CAC | ACC | CTA | AAG | CAT | TTC | 1536 |
| Tyr | Val | Arg | Ala | Glu | Gln | Lys | Asp | Arg | Gln | His | Thr | Leu | Lys | His | Phe | |
| | | | 500 | | | | | 505 | | | | | 510 | | | |
| GAG | CAT | GTG | CGC | ATG | GTG | GAT | CCC | AAG | AAA | GCC | GCT | CAG | ATC | CGG | TCC | 1584 |
| Glu | His | Val | Arg | Met | Val | Asp | Pro | Lys | Lys | Ala | Ala | Gln | Ile | Arg | Ser | |
| | | 515 | | | | | 520 | | | | | 525 | | | | |
| CAG | GTT | ATG | ACA | CAC | CTC | CGT | GTG | ATT | TAT | GAG | CGC | ATG | AAT | CAG | TCT | 1632 |
| Gln | Val | Met | Thr | His | Leu | Arg | Val | Ile | Tyr | Glu | Arg | Met | Asn | Gln | Ser | |
| | 530 | | | | | 535 | | | | | 540 | | | | | |
| CTC | TCC | CTG | CTC | TAC | AAC | GTG | CCT | GCA | GTG | GCC | GAG | GAG | ATT | CAG | GAT | 1680 |
| Leu | Ser | Leu | Leu | Tyr | Asn | Val | Pro | Ala | Val | Ala | Glu | Glu | Ile | Gln | Asp | |
| 545 | | | | | 550 | | | | | 555 | | | | | 560 | |
| GAA | GTT | GAT | GAG | CTG | CTT | CAG | AAA | GAG | CAA | AAC | TAT | TCA | GAT | GAC | GTC | 1728 |
| Glu | Val | Asp | Glu | Leu | Leu | Gln | Lys | Glu | Gln | Asn | Tyr | Ser | Asp | Asp | Val | |
| | | | | 565 | | | | | 570 | | | | | 575 | | |
| TTG | GCC | AAC | ATG | ATT | AGT | GAA | CCA | AGG | ATC | AGT | TAC | GGA | AAC | GAT | GCT | 1776 |
| Leu | Ala | Asn | Met | Ile | Ser | Glu | Pro | Arg | Ile | Ser | Tyr | Gly | Asn | Asp | Ala | |
| | | | 580 | | | | | 585 | | | | | 590 | | | |
| CTC | ATG | CCA | TCT | TTG | ACC | GAA | ACG | AAA | ACC | ACC | GTG | GAG | CTC | CTT | CCC | 1824 |
| Leu | Met | Pro | Ser | Leu | Thr | Glu | Thr | Lys | Thr | Thr | Val | Glu | Leu | Leu | Pro | |
| | | 595 | | | | | 600 | | | | | 605 | | | | |
| GTG | AAT | GGA | GAG | TTC | AGC | CTG | GAC | GAT | CTC | CAG | CCG | TGG | CAT | TCT | TTT | 1872 |
| Val | Asn | Gly | Glu | Phe | Ser | Leu | Asp | Asp | Leu | Gln | Pro | Trp | His | Ser | Phe | |
| | 610 | | | | | 615 | | | | | 620 | | | | | |
| GGG | GCT | GAC | TCT | GTG | CCA | GCC | AAC | ACA | GAA | AAC | GAA | GTT | GAG | CCT | GTT | 1920 |
| Gly | Ala | Asp | Ser | Val | Pro | Ala | Asn | Thr | Glu | Asn | Glu | Val | Glu | Pro | Val | |
| 625 | | | | | 630 | | | | | 635 | | | | | 640 | |
| GAT | GCC | CGC | CCT | GCT | GCC | GAC | CGA | GGA | CTG | ACC | ACT | CGA | CCA | GGT | TCT | 1968 |
| Asp | Ala | Arg | Pro | Ala | Ala | Asp | Arg | Gly | Leu | Thr | Thr | Arg | Pro | Gly | Ser | |
| | | | | 645 | | | | | 650 | | | | | 655 | | |
| GGG | TTG | ACA | AAT | ATC | AAG | ACG | GAG | GAG | ATC | TCT | GAA | GTG | AAG | ATG | GAT | 2016 |
| Gly | Leu | Thr | Asn | Ile | Lys | Thr | Glu | Glu | Ile | Ser | Glu | Val | Lys | Met | Asp | |
| | | | 660 | | | | | 665 | | | | | 670 | | | |

| | | | | | | | | | | | | | | | | |
|---|---|---|---|---|---|---|---|---|---|---|---|---|---|---|---|---|
| GCA | GAA | TTC | CGA | CAT | GAC | TCA | GGA | TAT | GAA | GTT | CAT | CAT | CAA | AAA | TTG | 2064 |
| Ala | Glu | Phe | Arg | His | Asp | Ser | Gly | Tyr | Glu | Val | His | His | Gln | Lys | Leu | |
| | | 675 | | | | 680 | | | | | | 685 | | | | |
| GTG | TTC | TTT | GCA | GAA | GAT | GTG | GGT | TCA | AAC | AAA | GGT | GCA | ATC | ATT | GGA | 2112 |
| Val | Phe | Phe | Ala | Glu | Asp | Val | Gly | Ser | Asn | Lys | Gly | Ala | Ile | Ile | Gly | |
| | 690 | | | | | 695 | | | | | 700 | | | | | |
| CTC | ATG | GTG | GGC | GGT | GTT | GTC | ATA | GCG | ACA | GTG | ATC | GTC | ATC | ACC | TTG | 2160 |
| Leu | Met | Val | Gly | Gly | Val | Val | Ile | Ala | Thr | Val | Ile | Val | Ile | Thr | Leu | |
| 705 | | | | | 710 | | | | | 715 | | | | | 720 | |
| GTG | ATG | CTG | AAG | AAG | AAA | CAG | TAC | ACA | TCC | ATT | CAT | CAT | GGT | GTG | GTG | 2208 |
| Val | Met | Leu | Lys | Lys | Lys | Gln | Tyr | Thr | Ser | Ile | His | His | Gly | Val | Val | |
| | | | | 725 | | | | 730 | | | | | 735 | | | |
| GAG | GTT | GAC | GCC | GCT | GTC | ACC | CCA | GAG | GAG | CGC | CAC | CTG | TCC | AAG | ATG | 2256 |
| Glu | Val | Asp | Ala | Ala | Val | Thr | Pro | Glu | Glu | Arg | His | Leu | Ser | Lys | Met | |
| | | | 740 | | | | | 745 | | | | | 750 | | | |
| CAG | CAG | AAC | GGC | TAC | GAA | AAT | CCA | ACC | TAC | AAG | TTC | TTT | GAG | CAG | ATG | 2304 |
| Gln | Gln | Asn | Gly | Tyr | Glu | Asn | Pro | Thr | Tyr | Lys | Phe | Phe | Glu | Gln | Met | |
| | | 755 | | | | | 760 | | | | | 765 | | | | |
| CAG | AAC | TAG | | | | | | | | | | | | | | 2313 |
| Gln | Asn | | | | | | | | | | | | | | | |
| | 770 | | | | | | | | | | | | | | | |

( 2 ) INFORMATION FOR SEQ ID NO: 8:

( i ) SEQUENCE CHARACTERISTICS:
        ( A ) LENGTH: 770 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 8:

| | | | | | | | | | | | | | | |
|---|---|---|---|---|---|---|---|---|---|---|---|---|---|---|
| Met | Leu | Pro | Gly | Leu | Ala | Leu | Leu | Leu | Ala | Ala | Trp | Thr | Ala | Arg |
| 1 | | | | 5 | | | | | 10 | | | | | 15 |
| Ala | Leu | Glu | Val | Pro | Thr | Asp | Gly | Asn | Ala | Gly | Leu | Leu | Ala | Glu | Pro |
| | | | 20 | | | | | 25 | | | | | 30 | | |
| Gln | Ile | Ala | Met | Phe | Cys | Gly | Arg | Leu | Asn | Met | His | Met | Asn | Val | Gln |
| | | 35 | | | | | 40 | | | | | 45 | | | |
| Asn | Gly | Lys | Trp | Asp | Ser | Asp | Pro | Ser | Gly | Thr | Lys | Thr | Cys | Ile | Asp |
| | 50 | | | | | 55 | | | | | 60 | | | | |
| Thr | Lys | Glu | Gly | Ile | Leu | Gln | Tyr | Cys | Gln | Glu | Val | Tyr | Pro | Glu | Leu |
| 65 | | | | | 70 | | | | | 75 | | | | | 80 |
| Gln | Ile | Thr | Asn | Val | Val | Glu | Ala | Asn | Gln | Pro | Val | Thr | Ile | Gln | Asn |
| | | | | 85 | | | | | 90 | | | | | 95 | |
| Trp | Cys | Lys | Arg | Gly | Arg | Lys | Gln | Cys | Lys | Thr | His | Pro | His | Phe | Val |
| | | | | 100 | | | | | 105 | | | | | 110 | |
| Ile | Pro | Tyr | Arg | Cys | Leu | Val | Gly | Glu | Phe | Val | Ser | Asp | Ala | Leu | Leu |
| | | | 115 | | | | | 120 | | | | | 125 | | |
| Val | Pro | Asp | Lys | Cys | Lys | Phe | Leu | His | Gln | Glu | Arg | Met | Asp | Val | Cys |
| | | 130 | | | | | 135 | | | | | 140 | | | |
| Glu | Thr | His | Leu | His | Trp | His | Thr | Val | Ala | Lys | Glu | Thr | Cys | Ser | Glu |
| 145 | | | | | 150 | | | | | 155 | | | | | 160 |
| Lys | Ser | Thr | Asn | Leu | His | Asp | Tyr | Gly | Met | Leu | Leu | Pro | Cys | Gly | Ile |
| | | | | 165 | | | | | 170 | | | | | 175 | |
| Asp | Lys | Phe | Arg | Gly | Val | Glu | Phe | Val | Cys | Cys | Pro | Leu | Ala | Glu | Glu |
| | | | 180 | | | | | 185 | | | | | 190 | | |
| Ser | Asp | Asn | Val | Asp | Ser | Ala | Asp | Ala | Glu | Glu | Asp | Asp | Ser | Asp | Val |
| | | | | 195 | | | | | 200 | | | | | 205 | |
| Trp | Trp | Gly | Gly | Ala | Asp | Thr | Asp | Tyr | Ala | Asp | Gly | Ser | Glu | Asp | Lys |

-continued

| | | | | 210 | | | | 215 | | | | 220 | | |
|---|---|---|---|---|---|---|---|---|---|---|---|---|---|---|
| Val 225 | Val | Glu | Val | Ala | Glu 230 | Glu | Glu | Val | Ala 235 | Glu | Val | Glu | Glu | Glu 240 |
| Glu | Ala | Asp | Asp | Asp 245 | Glu | Asp | Asp | Glu 250 | Gly | Asp | Glu | Val 255 | Glu | Glu |
| Glu | Ala | Glu | Glu 260 | Pro | Tyr | Glu | Glu | Ala 265 | Thr | Glu | Arg | Thr 270 | Thr | Ser | Ile |
| Ala | Thr | Thr 275 | Thr | Thr | Thr | Thr | Thr 280 | Glu | Ser | Val | Glu | Glu 285 | Val | Val | Arg |
| Glu | Val 290 | Cys | Ser | Glu | Gln | Ala 295 | Glu | Thr | Gly | Pro | Cys 300 | Arg | Ala | Met | Ile |
| Ser 305 | Arg | Trp | Tyr | Phe | Asp 310 | Val | Thr | Glu | Gly | Lys 315 | Cys | Ala | Pro | Phe | Phe 320 |
| Tyr | Gly | Gly | Cys | Gly 325 | Gly | Asn | Arg | Asn | Asn 330 | Phe | Asp | Thr | Glu | Glu 335 | Tyr |
| Cys | Met | Ala | Val 340 | Cys | Gly | Ser | Ala | Met 345 | Ser | Gln | Ser | Leu | Leu 350 | Lys | Thr |
| Thr | Gln | Glu 355 | Pro | Leu | Ala | Arg | Asp 360 | Pro | Val | Lys | Leu | Pro 365 | Thr | Thr | Ala |
| Ala | Ser | Thr 370 | Pro | Asp | Ala | Val 375 | Asp | Lys | Tyr | Leu | Glu 380 | Thr | Pro | Gly | Asp |
| Glu 385 | Asn | Glu | His | Ala | His 390 | Phe | Gln | Lys | Ala | Lys 395 | Glu | Arg | Leu | Glu | Ala 400 |
| Lys | His | Arg | Glu | Arg 405 | Met | Ser | Gln | Val | Met 410 | Arg | Glu | Trp | Glu | Glu 415 | Ala |
| Glu | Arg | Gln | Ala 420 | Lys | Asn | Leu | Pro | Lys 425 | Ala | Asp | Lys | Lys | Ala 430 | Val | Ile |
| Gln | His | Phe 435 | Gln | Glu | Lys | Val | Glu 440 | Ser | Leu | Glu | Gln | Glu 445 | Ala | Ala | Asn |
| Glu | Arg | Gln 450 | Gln | Leu | Val | Glu 455 | Thr | His | Met | Ala | Arg 460 | Val | Glu | Ala | Met |
| Leu 465 | Asn | Asp | Arg | Arg | Arg 470 | Leu | Ala | Leu | Glu | Asn 475 | Tyr | Ile | Thr | Ala | Leu 480 |
| Gln | Ala | Val | Pro | Pro 485 | Arg | Pro | Arg | His | Val 490 | Phe | Asn | Met | Leu | Lys 495 | Lys |
| Tyr | Val | Arg | Ala 500 | Glu | Gln | Lys | Asp | Arg 505 | Gln | His | Thr | Leu | Lys 510 | His | Phe |
| Glu | His | Val 515 | Arg | Met | Val | Asp | Pro 520 | Lys | Lys | Ala | Ala | Gln 525 | Ile | Arg | Ser |
| Gln | Val | Met 530 | Thr | His | Leu | Arg 535 | Val | Ile | Tyr | Glu | Arg 540 | Met | Asn | Gln | Ser |
| Leu 545 | Ser | Leu | Leu | Tyr | Asn 550 | Val | Pro | Ala | Val | Ala 555 | Glu | Glu | Ile | Gln | Asp 560 |
| Glu | Val | Asp | Glu | Leu 565 | Leu | Gln | Lys | Glu | Gln 570 | Asn | Tyr | Ser | Asp 575 | Asp | Val |
| Leu | Ala | Asn | Met 580 | Ile | Ser | Glu | Pro | Arg 585 | Ile | Ser | Tyr | Gly | Asn 590 | Asp | Ala |
| Leu | Met | Pro 595 | Ser | Leu | Thr | Glu | Thr 600 | Lys | Thr | Thr | Val | Glu 605 | Leu | Leu | Pro |
| Val | Asn 610 | Gly | Glu | Phe | Ser | Leu 615 | Asp | Asp | Leu | Gln | Pro 620 | Trp | His | Ser | Phe |
| Gly 625 | Ala | Asp | Ser | Val | Pro 630 | Ala | Asn | Thr | Glu | Asn 635 | Glu | Val | Glu | Pro | Val 640 |

| | | | | | | | | | | | | | | |
|---|---|---|---|---|---|---|---|---|---|---|---|---|---|---|
| Asp | Ala | Arg | Pro | Ala | Ala | Asp | Arg | Gly | Leu | Thr | Thr | Arg | Pro | Gly | Ser |
| | | | | 645 | | | | 650 | | | | | | 655 |
| Gly | Leu | Thr | Asn | Ile | Lys | Thr | Glu | Glu | Ile | Ser | Glu | Val | Lys | Met | Asp |
| | | | 660 | | | | | 665 | | | | | 670 | | |
| Ala | Glu | Phe | Arg | His | Asp | Ser | Gly | Tyr | Glu | Val | His | His | Gln | Lys | Leu |
| | | 675 | | | | | 680 | | | | | 685 | | | |
| Val | Phe | Phe | Ala | Glu | Asp | Val | Gly | Ser | Asn | Lys | Gly | Ala | Ile | Ile | Gly |
| | 690 | | | | | 695 | | | | | 700 | | | | |
| Leu | Met | Val | Gly | Gly | Val | Val | Ile | Ala | Thr | Val | Ile | Val | Ile | Thr | Leu |
| 705 | | | | | 710 | | | | | 715 | | | | | 720 |
| Val | Met | Leu | Lys | Lys | Lys | Gln | Tyr | Thr | Ser | Ile | His | His | Gly | Val | Val |
| | | | | 725 | | | | | 730 | | | | | 735 | |
| Glu | Val | Asp | Ala | Ala | Val | Thr | Pro | Glu | Glu | Arg | His | Leu | Ser | Lys | Met |
| | | | 740 | | | | | 745 | | | | | 750 | | |
| Gln | Gln | Asn | Gly | Tyr | Glu | Asn | Pro | Thr | Tyr | Lys | Phe | Phe | Glu | Gln | Met |
| | | 755 | | | | | 760 | | | | | 765 | | | |
| Gln | Asn | | | | | | | | | | | | | | |
| | 770 | | | | | | | | | | | | | | |